US012320814B2

(12) United States Patent
Jiang et al.

(10) Patent No.: US 12,320,814 B2
(45) Date of Patent: Jun. 3, 2025

(54) CHARACTERIZATION OF ADENO-ASSOCIATED VIRUS USING MICROCHIP CAPILLARY ELECTROPHORESIS

(71) Applicant: Regeneron Pharmaceuticals, Inc., Tarrytown, NY (US)

(72) Inventors: Bowen Jiang, White Plains, NY (US); Franco Tzul, Hartsdale, NY (US); Dingjiang Liu, Pleasantville, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 78 days.

(21) Appl. No.: 17/460,194

(22) Filed: Aug. 28, 2021

(65) Prior Publication Data

US 2022/0065868 A1  Mar. 3, 2022

Related U.S. Application Data

(60) Provisional application No. 63/071,815, filed on Aug. 28, 2020.

(51) Int. Cl.
  *G01N 33/68* (2006.01)
  *G01N 1/44* (2006.01)
  (Continued)

(52) U.S. Cl.
  CPC ........... *G01N 33/6839* (2013.01); *G01N 1/44* (2013.01); *G01N 27/44791* (2013.01); *G01N 33/58* (2013.01); *G01N 2333/015* (2013.01)

(58) Field of Classification Search
  CPC ................. G01N 33/6839; G01N 1/44; G01N 27/44791; G01N 33/58; G01N 2333/015; G01N 33/6803
  See application file for complete search history.

(56) References Cited

U.S. PATENT DOCUMENTS

2019/0086423 A1* 3/2019 Jarrold ............... G01N 33/6848

FOREIGN PATENT DOCUMENTS

WO  WO/2005033687 A1  4/2005

OTHER PUBLICATIONS

Chodankar, S., et al. "Structural Evolution during Protein Denaturation as Induced by Different Methods." Physical Review E, vol. 77, No. 3, 2008, https://doi.org/10.1103/physreve.77.031901 (Year: 2008).*

(Continued)

*Primary Examiner* — Jennifer Wecker
*Assistant Examiner* — Britney N. Washington
(74) *Attorney, Agent, or Firm* — McCarter & English, LLP; John P. Isacson (57) ABSTRACT

Methods and systems for identifying capsid viral proteins in a sample containing viral vectors are provided, including determining the ratio of the capsid viral proteins of adeno-associated virus. The methods and systems comprise denaturing the capsid viral proteins in the sample, labelling the denatured capsid viral proteins with a lysine-conjugation dye, generating a separation profile of the denatured/labelled capsid viral proteins using microchip capillary electrophoresis, quantifying levels of the capsid viral proteins based on the separation profile, determining a quantification ratio of the capsid viral proteins based on the separation profile, and normalizing the quantification ratio based on lysine contents of the capsid viral proteins.

9 Claims, 8 Drawing Sheets

(51) Int. Cl.
G01N 27/447 (2006.01)
G01N 33/58 (2006.01)

(56) References Cited

OTHER PUBLICATIONS

Weiss et al. "Virus analysis by electrophoresis on a microfluidic chip." Journal of chromatography. B, Analytical technologies in the biomedical and life sciences vol. 860, No. 2 (2007): pp. 173-179. https://doi.org/10.1016/j.jchromb.2007.10.026 (Year: 2007).*

Pappas, Diane E., and J. Owen Hendley. "The Common Cold." Principles and Practice of Pediatric Infectious Disease, 2008, pp. 203-206., https://doi.org/10.1016/b978-0-7020-3468-8.50034-1 (Year: 2008).*

Van Tricht, Ewoud, et al. "New capillary gel electrophoresis method for fast and accurate identification and quantification of multiple viral proteins in influenza vaccines." Talanta, vol. 144, Jul. 21, 2015, pp. 1030-1035, https://doi.org/10.1016/j.talanta.2015.07.047 (Year: 2015).*

Weiss et al: "Virus analysis by electrophoresis on a microfluidic chip", Journal of Chromatography B, Elsevier, Amsterdam, NL, vol. 860, No. 2, Nov. 19, 2007 (Nov. 19, 2007), pp. 173-179.

Tanigawa K et al: "On-Line Preconcentration Using Denaturation of Proteins on a Heater Integrated Electrophoresis Microchip", Jan. 1, 2010 (Jan. 1, 2010), XP055859578, Retrieved from the Internet: URL:https://www.rsc.org/binaries/LOC/2010/PDFs/Papers/3550266.pdf.

Xiaoying Jin et al: "Direct Liquid Chromatography/Mass Spectrometry Analysis for Complete Characterization of Recombinant Adeno-Associated Virus Capsid Proteins", Human Gene Therapy Methods, Jun. 16, 2017 (Jun. 16, 2017).

Schuler B et al: "Specific labeling of polypeptides at amino-terminal cysteine residues using Cy5-benzyl thioester", Bioconjugate Chemistry, American Chemical Society, US, vol. 13, No. 5, Jul. 18, 2002 (Jul. 18, 2002), pp. 1039-1043.

Henry Charles S: "Microchip capillary electrophoresis—An introduction", Methods in Molecular Biology Humana Press Inc, 999 Riverview Dr, STE 208, Totowa, NJ 07512-1165 USA Series : Methods in Molecular Biology (ISSN 1064-3745(PRINT)), 2006, pp. 1-9.

International Application No. PCT/US2021/048116, International Filing Date Aug. 28, 2021, International Search Report dated Nov. 18, 2021.

* cited by examiner

CHARACTERIZATION OF ADENO-ASSOCIATED VIRUS USING MICROCHIP CAPILLARY ELECTROPHORESIS

CROSS-REFERENCE TO RELATED APPLICATION

This application claims priority to and the benefit of U.S. Provisional Patent Application No. 63/071,815, filed Aug. 28, 2020 which is herein incorporated by reference.

FIELD

The present invention generally pertains to methods and systems for characterizing or quantifying capsid proteins of adeno-associated virus using microchip capillary electrophoresis in combination with fluorescent dye.

BACKGROUND

Gene therapy biopharmaceuticals mediate therapeutic effects by transcription and/or translation of transferred genetic material, such as integrating genetic material into the host genome. Gene therapy biopharmaceuticals include nucleic acids, plasmids, viruses, vectors, or genetically engineered microorganisms. Adeno-associated viruses (AAV) have been widely used as gene delivery vectors to deliver genetic material for gene therapy. Although AAVs do not integrate into the host genome, AAVs can provide long-term gene expression in non-dividing cells.

During manufacturing of biopharmaceutical products, product evaluation includes assessing the components used in manufacturing, testing/characterizing final products and evaluating control of the manufacturing processes to ensure product safety and quality. The final product should be tested and characterized for purity, identity and potency. Thus, the product tests for AAVs can include testing the ratio of infectious to non-infectious vectors, the presence of empty capsids, or the stoichiometric ratios of viral proteins. Characterizing AAV capsid proteins is critical to ensure product quality and consistency of AAVs from lot to lot, since the assembly of viral capsid proteins of AAVs can have significant impact on AAV infectivity, potency and stability.

It will be appreciated that a need exists for methods and systems to identify and characterize capsid viral proteins of AAVs. Characterizations of capsid viral proteins of AAVs should include determining the ratios of different capsid viral proteins, since the correct ratio of capsid viral proteins can be critical to biological functions of AAVs (specifically, the capsid structure along with the amino acid differences that mediate tissue tropisms). These methods and systems should provide robust, rapid, reliable, sensitive and high throughput detection and characterization of the capsid viral proteins of AAVs.

SUMMARY

The present application provides methods and systems for identifying and/or characterizing capsid viral proteins in a sample containing viral vectors. These methods and systems provide rapid, reliable, sensitive and high throughput processes to identify the capsid viral proteins, including determining the ratios of different capsid viral proteins of AAVs.

This disclosure provides a method of determining a quantification ratio between two or more proteins in a sample containing viral vectors. In some exemplary embodiments, this disclosure provides a method comprising: denaturing two or more proteins in a sample in a denaturation solution at a temperature of at least about 60° C.; labelling the denatured two or more proteins with a lysine-conjugation dye; generating a separation profile of the denatured/labelled two or more proteins using microchip capillary electrophoresis; quantifying levels of the two or more proteins based on the separation profile; and comparing the quantified levels of the two or more proteins to determine a quantification ratio between said two or more proteins.

In one aspect, the method of the present application further comprises normalizing the quantification ratio based on lysine contents of the two or more proteins. In one aspect, the method of the present application further comprises correcting the quantification ratio based on a migration time of the separation profile. In one aspect, the lysine-conjugation dye of the method of the present application is an amine-reactive fluorescent dye. In another aspect, the lysine-conjugation dye of the method of the present application comprises an active ester, an isothiocyanate, or a sulfonyl chloride. In yet another aspect, the lysine-conjugation dye of the method of the present application comprises an active ester, wherein the active ester includes a succinimidyl ester, a sulfosuccinimidyl ester, a tetrafluorophenyl ester, or a sulfodichlorophenol ester.

In one aspect, the viral vector of the method of the present application is an AAV. In one aspect, the viral vector of the method of the present application comprises viral protein 1 (VP1), viral protein 2 (VP2) and viral protein 3 (VP3). In another aspect, the denaturation solution of the method of the present application comprises a detergent, wherein the detergent is lithium dodecyl sulfate (LDS) or sodium dodecyl sulfate (SDS).

This disclosure, at least in part, provides a system for determining a quantification ratio between two or more proteins in a sample containing at least one viral vector. In some exemplary embodiments, this disclosure provides a system comprising: a microplate for receiving a sample containing at least one viral vector, a denaturation solution capable of denaturing two or more proteins in said sample at a temperature of at least about 60° C., and a lysine-conjugation dye capable of labelling the two or more proteins; and a microchip capillary electrophoresis device capable of receiving said microplate, separating the denatured/labelled two or more proteins to generate a separation profile, quantifying levels of the two or more proteins, and comparing the quantified levels of the two or more proteins to determine a quantification ratio between the two or more proteins.

In one aspect, the quantification ratio can be normalized based on lysine contents of the two or more proteins. In one aspect, the quantification ratio can be corrected based on a migration time of the separation profile. In another aspect, the lysine-conjugation dye of the system of the present application is an amine-reactive fluorescent dye. In one aspect, the lysine-conjugation dye of the system of the present application comprises an active ester, an isothiocyanate, or a sulfonyl chloride. In yet another aspect, the lysine-conjugation dye of the system of the present application comprises an active ester, wherein the active ester includes a succinimidyl ester, a sulfosuccinimidyl ester, a tetrafluorophenyl ester, or a sulfodichlorophenol ester.

In one aspect, the viral vector of the system of the present application is an AAV. In one aspect, the viral vector of the system of the present application comprises VP1, VP2 and VP3. In another aspect, the denaturation solution of the system of the present application comprises a detergent, wherein the detergent is LDS or SDS.

These, and other, aspects of the invention will be better appreciated and understood when considered in conjunction with the following description and the accompanying drawings. The following description, while indicating various embodiments and numerous specific details thereof, is given by way of illustration and not of limitation. Many substitutions, modifications, additions, or rearrangements may be made within the scope of the invention.

DETAILED DESCRIPTION

Figure 1A:
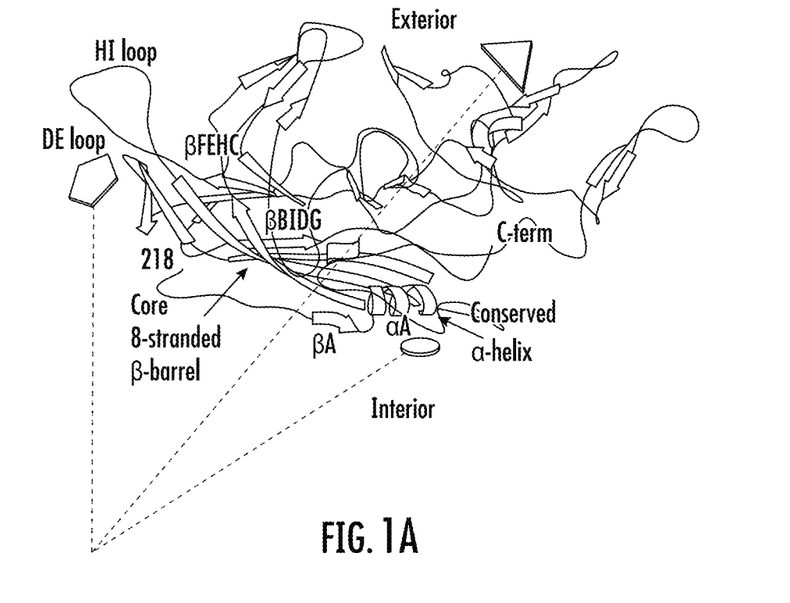
FIG. 1A shows the structure of AAV1 including a crystal structure of AAV1 capsid VP3 monomer and FIG. 1B shows a surface representation of AAV1 capsid according to Venkatakrishnan et al., Structure and Dynamics of Adeno-Associated Virus Serotype 1 VP1-Unique N-Terminal Domain and Its Role in Capsid Trafficking, Journal of Virology, May 2013, vol. 87, no. 9, pages 4974-4984.
Figure 1B:
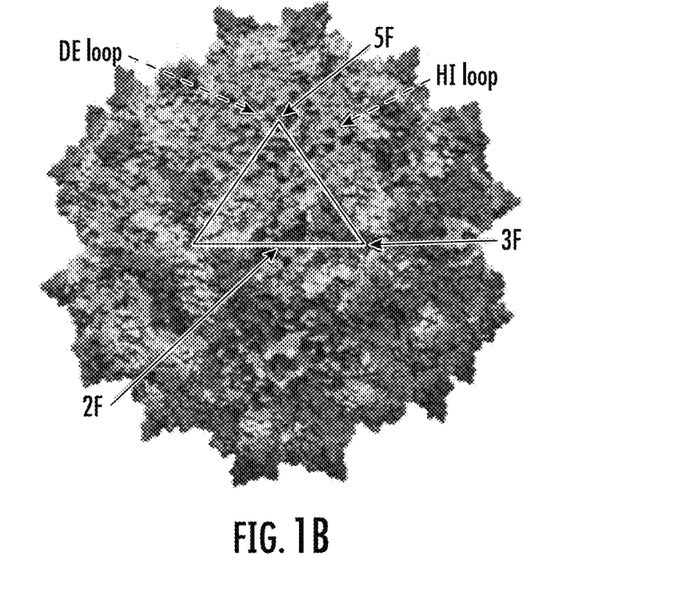

Adeno-associated viruses (AAVs) have been widely used as gene delivery vectors to deliver genetic material, such as delivering nucleic acids for gene therapy. AAVs provide the advantages of non-pathogenicity and low immunogenicity. AAVs are nonpathogenic members of the Parvoviridae family under Dependovirus genus and require helpers, such as Adenovirus or Herpesvirus, for infection (Venkatakrishnan et al., Structure and Dynamics of Adeno-Associated Virus Serotype 1 VP1-Unique N-Terminal Domain and Its Role in Capsid Trafficking, Journal of Virology, May 2013, vol. 87, no. 9, pages 4974-4984). AAV encapsulates a single-stranded DNA genome of about 4.8 kilobases (kb) in an icosahedral capsid which is made of a shell of proteins, for example, capsid viral proteins. FIG. 1A shows the structure of AAV1 including a crystal structure of AAV1 capsid VP3 monomer and FIG. 1B shows surface representation of AAV1 capsid (Venkatakrishnan et al.).

In order to monitor the quality and efficiency of AAVs as gene delivery vectors, it is critical to monitor the purity, capsid identity, vector particle titer, empty/full ratio and capsid viral protein ratio. The capsid viral proteins self-assemble to form the outer capsid shell, which is actively involved in cell binding and cell entry. The capsid viral proteins self-assemble in a specific stoichiometric ratio which is important to the capsid shell's structure. Therefore, there is a critical need to develop a method which is rapid, reliable, sensitive and high throughput to determine the ratios of capsid viral proteins for AAVs to be used as gene delivery systems. The characterizations of AAV capsid proteins should include the ratios of different capsid proteins. The correct ratio of capsid viral proteins is critical to biological functions of AAVs. The degradation of capsid proteins can be detrimental to infectivity of AAVs. Capsids should be able to protect the AAV genome until a suitable host cell appears, cell entry is initiated, and the AAV genome is released for replication.

Characterizations of AAV capsid proteins are important to ensure the product quality and consistency of AAVs, since the assembly of viral capsid proteins of AAVs can have significant impacts on viral infectivity and vector potency (Jin et al., Direct liquid chromatography/mass spectrometry analysis for complete characterization of recombinant adeno-associated virus capsid proteins, Human gene therapy methods, 2017, Vol. 28, No. 5, pages 255-267). The capsid viral proteins of AAVs may play a role in the initiation of both second-strand synthesis when ssDNA is encased and transcription of the input genome (Salganik et al., Adeno-associated virus capsid proteins may play a role in transcription and second-strand synthesis of recombinant genomes, Journal of Virology, January 2014, Vol. 88, No. 2, pages 1071-1079).

The single-stranded AAV genome contains three genes including rep (replication), cap (capsid) and aap (assembly). The rep gene is relevant to viral genome replication and packaging. The cap gene encodes capsid viral proteins. The expression of the cap gene produces capsid viral proteins including VP1, VP2, and VP3, made from alternately spliced mRNAs with common C termini. VP3 is approximately 61 kDa and constitutes about 85% of the capsid protein contents. VP2 is approximately 73 kDa. VP1 is approximately 87 kDa. VP1 contains the VP1 unique region (VP1u) including a phospholipase A2 domain and nuclear localization signals. (Rayaprolu et al., Comparative analysis of adeno-associated virus capsid stability and dynamics, Journal of Virology, December 2013, vol. 87, No. 24, p. 13150-13160) The AAV capsid consists of 60 viral protein monomers including VP1, VP2, and VP3. VP3 is the major capsid protein, and thus plays a major role in the stability of the capsid shell. There are approximately 50 copies of VP3 in the AAV capsid. There are approximately 5 copies of VP1 and 5 copies of VP2 in the AAV capsid. In general, the ratio of VP1:VP2:VP3 is about 1:1:10 in the capsid containing 60 viral protein monomers, for example, 5 copies of VP1, 5 copies of VP2, and 50 copies of VP3. (Venkatakrishnan et al.)

Figure 2A:
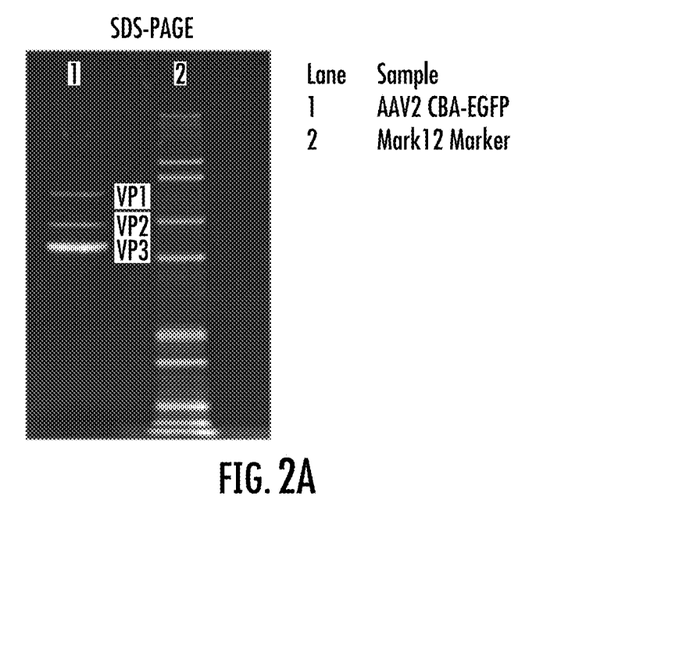
FIG. 2A shows the separation of capsid viral proteins of AAVs using conventional methods, such as SDS-PAGE
Figure 2B:
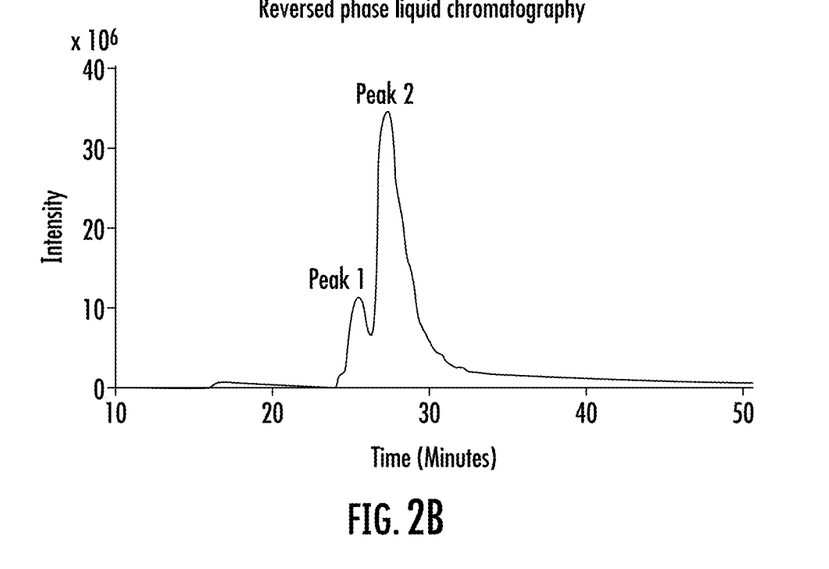
FIG. 2B shows reverse phase liquid chromatography, according to Jin et al., Direct liquid chromatography/mass spectrometry analysis for complete characterization of recombinant adeno-associated virus capsid proteins, Human gene therapy methods, 2017, vol. 28, No. 5, pages 255-267.

AAV capsid viral proteins can be separated based on size differences using SDS-PAGE (sodium dodecyl sulfate-polyacrylamide gel electrophoresis). Conventional analysis methods for characterizing AAV capsid proteins include SDS-PAGE analysis (FIG. 2A) and reverse phase liquid chromatography (as shown in FIG. 2B, according to Jin et al.). However, SDS-PAGE separation is low throughput with quantitative variations. VP1, VP2 and VP3 can be visualized using SDS-PAGE with silver stain which is a labor intensive and time consuming process with poor quantitative data. The issues of poor quantitative data derived from SDS-PAGE in combination with silver stain include sample overloading, gel overheating, and inadequate standardization of staining/destaining. Another approach is to combine SDS-PAGE separation with in-gel enzymatic digestion and liquid chromatography/tandem mass spectrometry (LC-MS/MS) to characterize the capsid viral proteins. However, there are limitations on this method due to the limited recovery of digested peptides from the gel. In addition, reverse phase liquid chromatography is not sufficient to separate capsid proteins for certain serotypes. Significant viral protein overlap can occur, as well as poor baseline resolution of the viral proteins that do get separated. In addition, the separation time required per sample is approximately about 45 to about 60 minutes, which is low throughput for industry requirements. Jin et al. provides a direct LC/MS intact protein analysis to characterize capsid proteins in a variety of AAV serotypes by identifying N- and C-terminal sequences of several capsid proteins based on accurate mass measurement.

Capillary electrophoresis, such as microchip capillary electrophoresis, is an alternative technology to separate capsid viral proteins, which has higher throughput (about 42 to 65 seconds per sample) with automation. UV detection is commonly associated with capillary electrophoresis for protein detection. However, UV detection has lower sensitivity and requires a larger sample volume, especially for AAV drug products when protein concentration is typically less than 1 mg/mL. Alternative protein detection methods include column stacking of multiple injections or fluorescence detections. In addition, samples separated using capillary electrophoresis can be stained with fluorescent dyes binding to hydrophobic patches of sample. However, the binding of hydrophobic dye to protein is an uncontrolled staining stoichiometry, due to the varying degrees of hydrophobic patches, per serotype, available for the dye to bind. It is also difficult to quantify the hydrophobic patches in capsid proteins. Therefore, the ratio of capsid viral proteins cannot be estimated accurately using the method of capillary electrophoresis in combination with hydrophobic dye staining.

In some exemplary embodiments, the present application provides methods and systems to identify and/or characterize the capsid viral proteins of viral vectors including quantifying the ratio of capsid viral proteins of viral vectors using microchip capillary electrophoresis in combination with lysine-conjugation fluorescent dyes. In some exemplary embodiments, the present application provides a method for identifying and/or quantifying capsid viral proteins of viral vectors and the method comprises: denaturing capsid viral proteins of the viral vectors in a denaturation solution at a temperature of at least about 60° C., up to about 95° C., or typically about 75° C. for about 10 minutes, wherein the denaturation solution contains LDS; labelling the denatured capsid viral proteins with a lysine-conjugation dye; and generating a separation profile of the denatured/labelled capsid viral proteins using microchip capillary electrophoresis. In some aspects, the capsid viral proteins of the viral vectors are labeled with lysine-conjugation fluorescent dyes. In some aspects, the capsid viral proteins of viral vectors are labeled with amine-reactive fluorescent dyes comprising active esters, isothiocyanates, or sulfonyl chlorides. In some aspects, the active ester comprises succinimidyl esters, sulfosuccinimidyl esters, tetrafluorophenyl esters, or sulfodichlorophenol esters. In one aspect, the viral vector of the method of the present application is AAV comprising VP1, VP2 and VP3. In one aspect, the capsid viral proteins of the viral vectors can be labeled under reduced or non-reduced conditions. When the capsid viral proteins are labeled under reduced conditions, DTT (dithiothreitol) can be used as a reducing agent. When the capsid viral proteins are labeled under non-reduced conditions, alkylation agent, such as N-ethylmaleimide (NEM) or iodoacetamide (IAM), can be used.

In some exemplary embodiments, the present application provides a method for identifying capsid viral proteins in a sample containing viral vectors and the method comprises: denaturing the capsid viral proteins in a denaturation solution at a temperature of at least about 60° C.; labelling the denatured capsid viral proteins with a lysine-conjugation dye; generating a separation profile of the denatured/labelled capsid viral proteins using microchip capillary electrophoresis; quantifying levels of the capsid viral proteins based on the separation profile; and determining a quantification ratio of the capsid viral proteins based on the separation profile. In one aspect, the method of the present application further comprises normalizing the quantification ratio based on lysine contents of the capsid viral proteins and correcting the quantification ratio based on a migration time of the separation profile. In one aspect, the viral vector of the method of the present application is AAV comprising VP1, VP2 and VP3.

In some exemplary embodiments, the present application provides a system for identifying and/or determining a quantification ratio between proteins, for example capsid viral proteins, in a sample containing viral vectors. In some aspects, the present application provides a system comprising: a microplate for receiving a sample containing viral vectors, a denaturation solution capable of denaturing two or more proteins, for example capsid viral proteins, in said sample at a temperature of at least 60° C., wherein the denaturation solution contains LDS, and a lysine-conjugation dye capable of labelling the two or more proteins; and a microchip capillary electrophoresis device capable of receiving said microplate, separating the denatured/labelled two or more proteins to generate a separation profile, quantifying levels of the two or more proteins and comparing the quantified levels of the two or more proteins to determine a quantification ratio of the two or more proteins. In one aspect, the quantification ratio can be normalized based on lysine contents of the two or more capsid viral proteins. In one aspect, the quantification ratio can be normalized based on a migration time of the separation profile.

The demands of improving the product quality, consistency, efficacy and safety of biopharmaceutical products containing AAV have led to an increasing demand for identifying and/or characterizing capsid viral proteins of AAV. The present application provides methods and systems for identifying and/or characterizing capsid viral proteins in a sample containing viral vectors. The advantages of the methods and systems of the present application include providing methods and systems which are rapid, reliable, sensitive and high throughput to identify and/or characterize the capsid viral proteins of AAV, including determining the ratios of capsid viral proteins, to satisfy the aforementioned demands. Exemplary embodiments disclosed herein satisfy the aforementioned demands by providing methods and systems for identifying and/or characterizing capsid viral proteins of AAV to satisfy the long felt needs.

The term "a" should be understood to mean "at least one"; and the terms "about" and "approximately" should be understood to permit standard variation as would be understood by those of ordinary skill in the art; and where ranges are provided, endpoints are included. As used herein, the terms "include," "includes," and "including," are meant to be non-limiting and are understood to mean "comprise," "comprises," and "comprising," respectively.

In some exemplary embodiments, the present application provides a method for identifying and determining a quantification ratio between two or more proteins in a sample containing virus particles and the method comprises: denaturing the two or more proteins in the sample in a denaturation solution at a temperature of at least 60° C.; labelling the denatured two or more proteins with a lysine-conjugation dye; generating a separation profile of the denatured/labelled two or more proteins using microchip capillary electrophoresis; quantifying levels of the two or more proteins based on the separation profile; and determining a quantification ratio of the two or more proteins based on the separation profile.

As used herein, the term "microchip capillary electrophoresis" refers to an approach for high-speed separations of biomolecules in the presence of electroosmotic flow using open tubular electrophoresis, such as glass capillaries in a microfluidic format. Electroosmotic flow is a bulk solution flow phenomenon that occurs in capillaries filled with mild ionic solution when a voltage is established across the capillary. The velocity of a given analyte species during capillary electrophoresis separation is determined by the mobility of the analyte plus the electroosmotic flow. The electrophoretic mobility of the analyte molecules is a critical factor for separation, which can be influenced by the analyte mass and net charge. (Charles S. Henry, Microchip Capillary Electrophoresis: An Introduction, February 2006, Methods in Molecular Biology 339:1-10). In microchip capillary electrophoresis, voltages of the order of 1 kV are used, and with channel lengths from sub-millimeters to centimeters, this translates to 100 V/cm to 10 kV/cm.

As used herein, the term "vector" refers to a recombinant plasmid or virus that comprises a nucleic acid to be delivered into a host cell, either in vitro or in vivo. The vectors derived from AAV are particularly attractive for delivering genetic material because (i) they are able to infect (transduce) a wide variety of non-dividing and dividing cell types including muscle fibers and neurons; (ii) they are devoid of the virus structural genes, thereby eliminating the natural host cell responses to virus infection, for example, interferon-mediated responses; (iii) wild type AAVs have never been associated with any pathology in humans; (iv) in contrast to wild type AAVs, which are capable of integrating into the host cell genome, replication-deficient AAV vectors generally persist as episomes, thus limiting the risk of insertional mutagenesis or activation of oncogenes; and (v) in contrast to other vector systems, AAV vectors do not trigger a significant immune response (see ii), thus granting long-term expression of the therapeutic transgenes (provided their gene products are not rejected).

As used herein, the term "protein" includes any amino acid polymer having covalently linked amide bonds. Proteins comprise one or more amino acid polymer chains, generally known in the art as "peptide" or "polypeptides". A protein may contain one or multiple polypeptides to form a single functioning biomolecule.

EXEMPLARY EMBODIMENTS

Embodiments disclosed herein provide methods and systems for identifying and/or characterizing capsid viral proteins in a sample containing viral vectors.

In some exemplary embodiments, the present application provides a method for determining a quantification ratio between two or more capsid viral proteins in a sample containing viral vectors and the method comprises: denaturing the capsid viral proteins in the sample in a denaturation solution at a temperature of at least about 60° C.; labelling the denatured capsid viral proteins with a lysine-conjugation dye; generating a separation profile of the denatured/labelled capsid viral proteins using microchip capillary electrophoresis; quantifying levels of the capsid viral proteins based on the separation profile; comparing the quantified levels of the capsid viral proteins to determine a quantification ratio between the capsid viral proteins; and normalizing the quantification ratio of the capsid viral proteins based on the lysine contents of the capsid viral proteins.

In one aspect, the capsid viral proteins in the sample are denatured in a denaturation solution at a temperature of at least about 60° C., at least about 65° C., at least about 70° C., at least about 75° C., at least about 80° C., at least about 85° C., at least about 90° C., at least about 95° C., from about 60° C. to 95° C., from about 70° C. to 95° C., from about 75° C. to 95° C., from about 80° C. to 95° C., or from about 85° C. to 95° C. for about 3 minutes, about 4 minutes, about 5 minutes, about 6 minutes, about 7 minutes, about 8 minutes, about 9 minutes, or about 10 minutes. In another aspect, the capsid viral proteins in the sample can be denatured in a denaturation solution by heating in a stepwise manner from about 60° C. to 95° C., from about 70° C. to 95° C., from about 75° C. to 95° C., from about 80° C. to 95° C., or from about 85° C. to 95° C. for about 3 minutes, about 4 minutes, about 5 minutes, about 6 minutes, about 7 minutes, about 8 minutes, about 9 minutes, or about 10 minutes.

In one aspect, the lysine-conjugation dye of the method of the present application is an amine-reactive fluorescent dye containing an active ester, an isothiocyanate, or a sulfonyl chloride. In one aspect, the lysine-conjugation dye of the method of the present application comprises an active ester, wherein the active ester includes a succinimidyl ester, a sulfosuccinimidyl ester, a tetrafluorophenyl ester, or a sulfodichlorophenol ester.

It is understood that the system is not limited to any of the aforesaid AAV, microchip capillary electrophoresis device, capsid viral proteins, lysine-conjugation dye, or amine-reactive fluorescent dye. As described above, one of the benefits of the method and system of the present invention is that, unlike conventional methods such as the use of a hydrophobic dye, the use of a lysine-conjugation dye allows for accurate identification and quantification of any protein, as long as the number of lysines in the amino acid sequence is known. Thus, for example, while particular viruses may be exemplified, it is understood that the method and system of the present invention can be applied to other AAV serotypes and other viruses.

The consecutive labeling of method steps as provided herein with numbers and/or letters is not meant to limit the method or any embodiments thereof to the particular indicated order. Various publications, including patents, patent applications, published patent applications, accession numbers, technical articles and scholarly articles are cited throughout the specification. Each of these cited references is incorporated herein by reference, in its entirety and for all purposes. Unless described otherwise, all technical and scientific terms used herein have the same meaning as commonly understood by one of ordinary skill in the art to which this invention belongs. This disclosure will be more fully understood by reference to the following Examples, which are provided to describe this disclosure in greater detail. They are intended to illustrate and should not be construed as limiting the scope of this disclosure.

EXAMPLES

Reagents and Methods

1. Sample preparation, labelling and analysis using lysine-conjugation dye: The capsid viral proteins were labeled with fluorescent dyes using lysine-conjugation dyes or amine-reactive fluorescent dyes, such as Pico Protein Express labeling dye (PerkinElmer). The amine-reactive fluorescent dyes can react with primary amines by labeling lysine residues and N-terminal amines. After quenching the labeling reaction, the extent and position of the incorporated fluorescent dye was monitored. Proteins have variable contents of lysine residues which are available for labeling. Dye quantities and protein concentrations are titrated and optimized for labelling reactions.

Figure 3:
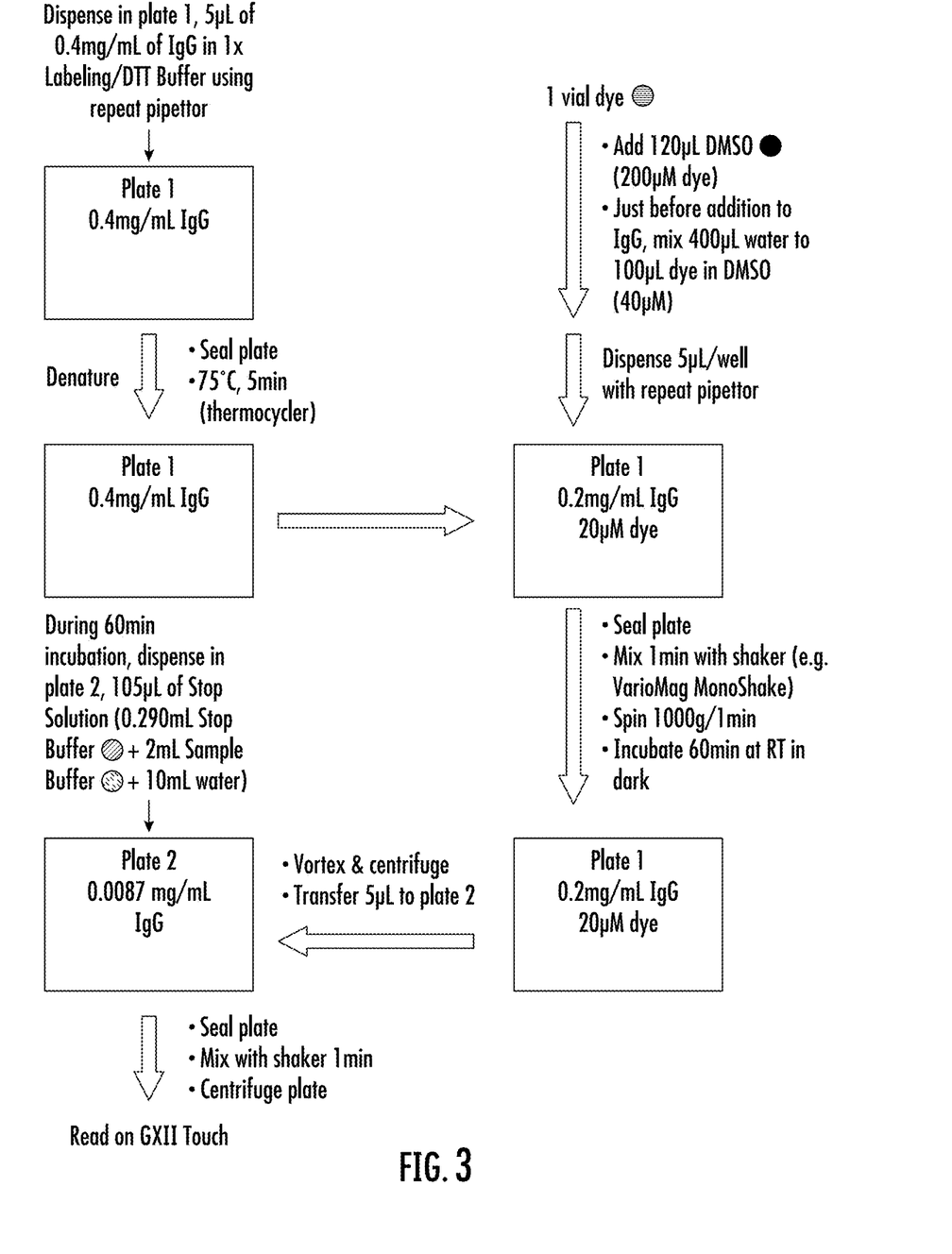
FIG. 3 shows the process for sample preparation to label proteins with lysine-conjugation dyes under reduced conditions according to an exemplary embodiment.
Figure 4:
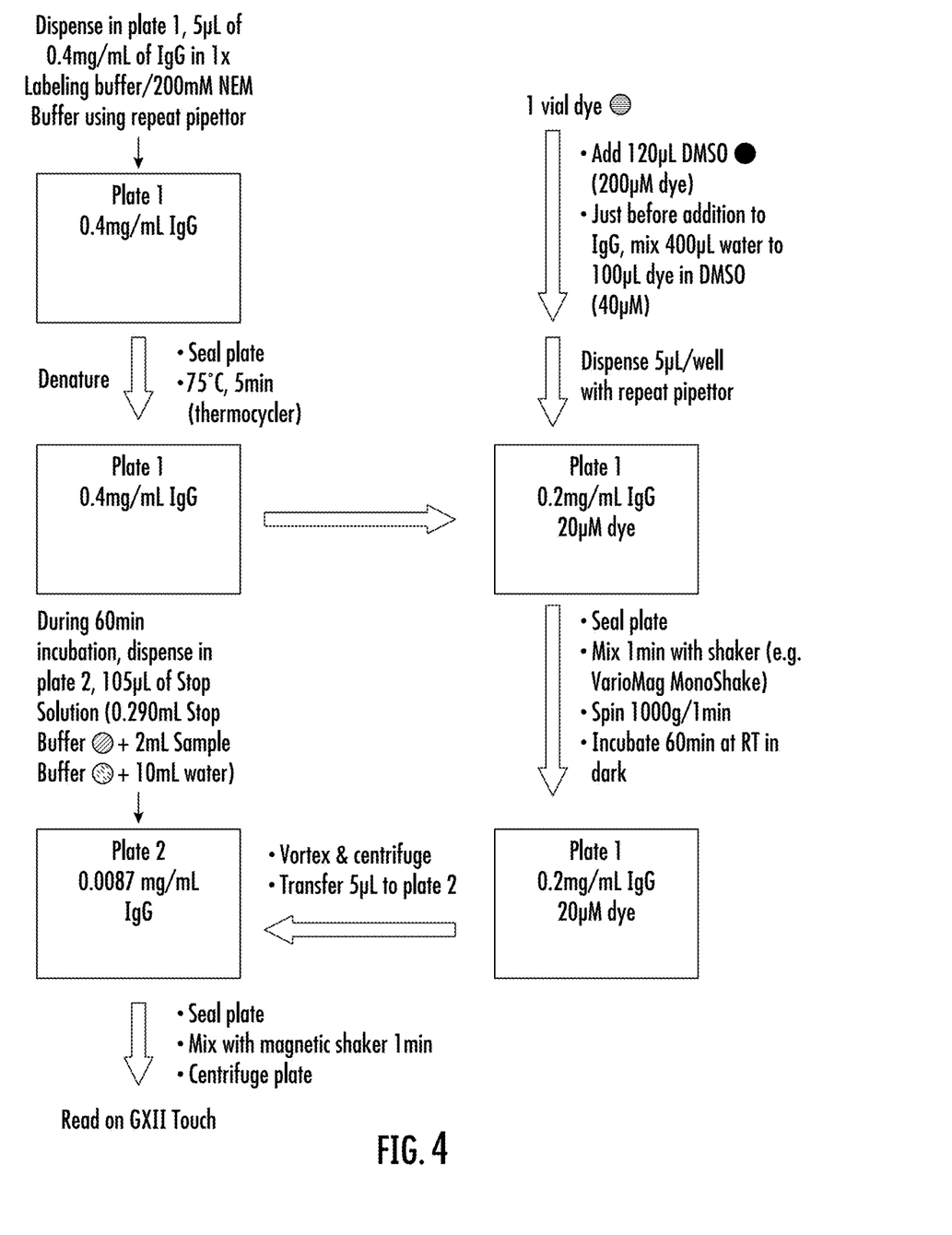
FIG. 4 shows the process for sample preparation to label proteins with lysine-conjugation dyes under non-reduced conditions according to an exemplary embodiment.

Pico Protein Express Assay reagent kit (PerkinElmer) was used to label protein samples having concentration ranges of 0.1-1 mg/mL in pH 6-9 buffer according to the user guide provided by the manufacturer (Pico Protein Express Assay User Guide for LabChip® GXII Touch, PerkinElmer, Hopkinton, MA). The labeling buffer containing a lysine-conjugation fluorescent dye was used for sample labeling. The composition of 1× labelling buffer of the Pico Protein Express Assay reagent kit for sample preparation is 0.1 M sodium bicarbonate, 0.14% LDS, pH 8. The sample buffer also contains LDS. The protein samples can be labeled under reduced or non-reduced conditions. In order to label protein sample under reduced conditions, DTT was used as a reducing agent as shown in FIG. 3 according to the manufacturer's instructions. FIG. 3 shows the process of sample preparation under reduced conditions by using IgG as an example. FIG. 4 shows the process for sample preparation to label proteins with lysine-conjugation dyes under non-reduced conditions by using IgG as an example according to the manufacturer's instructions. Alkylation agent, such as NEM or iodoacetamide, may be used for non-reduced conditions.

The labelled protein samples containing capsid viral proteins were loaded on a microfluidic chip to be analyzed using LabChip® GXII, LabChip® GXII Touch or LabChip® GXII Touch HT using fluorescence detection. Appropriate assay types were selected from the assay list provided by the instruments. Pico Protein Express 100 was selected for sizing proteins in the 14-100 kDa range. Pico Protein Express 200 was selected for sizing proteins in the 14-200 kDa range. The assay function of the instrument can determine protein concentration based on alignment and scaling with protein standards. After alignment, the size of each protein peak is calculated from the aligned peak time using a log (size) versus 1/Time fit to the primary ladder peaks of known size and measured migration time. To determine sample peak concentration, the peak areas are first corrected to compensate for fluorescence intensities. The fluorescence intensities are sampled at a constant time interval, so slower moving proteins spend more time under the detector than fast moving proteins. The peak concentration can then be calculated using the ladder peak areas and concentration for the ladder supplied in the Assay Analysis window. The concentration is adjusted for the dilution factors of sample and ladder. (Pico Protein Express Assay User Guide for LabChip® GXII Touch, PerkinElmer, Hopkinton, MA)

Figure 5:
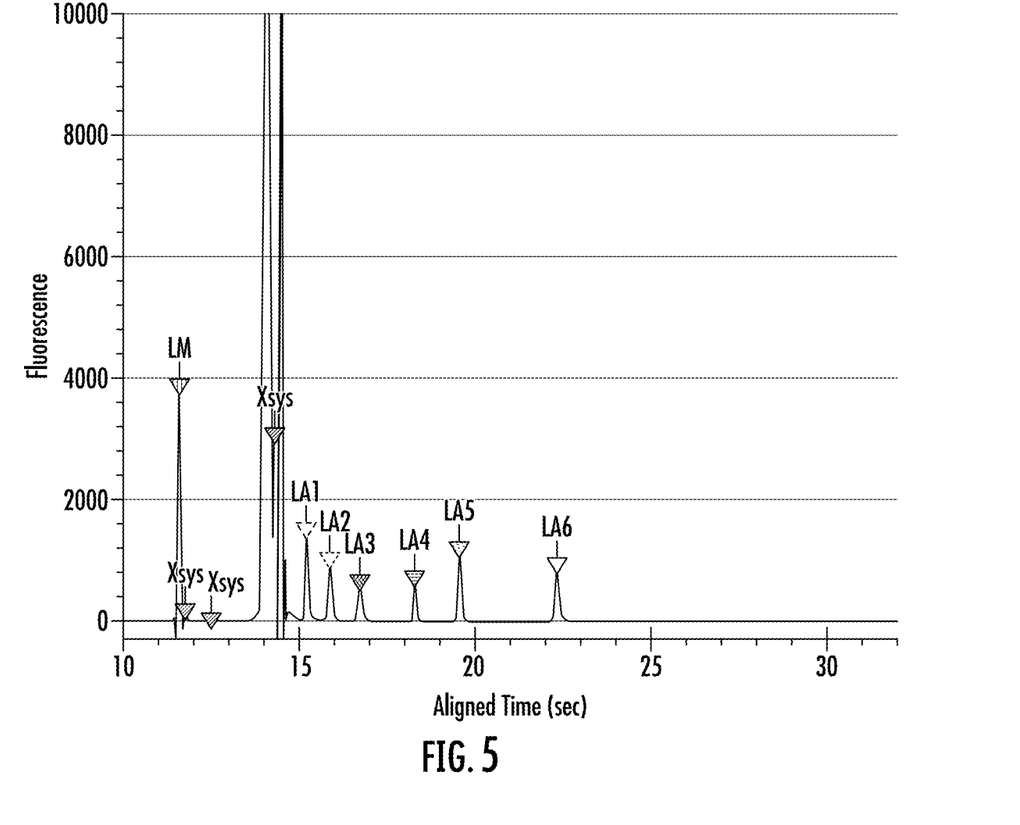
FIG. 5 shows a Pico Protein Express ladder containing six protein standards having molecular weights of 15.9 kDa (LA1), 20.4 kDa (LA2), 28.9 kDa (LA3), 48.4 kDa (LA4), 68.4 kDa (LA5) or 119.2 kDa (LA6) according to an exemplary embodiment.

2. Protein molecular weight standard: Pico Protein Express ladder (PerkinElmer) was used to calibrate or estimate the molecular weight of the AAV capsid viral proteins. The protein ladders were prepared in series dilution in the range of from 7.8 ng/µL to 250 ng/µL using 1:2 fold dilution. Six protein standards having molecular weights of 15.9 kDa (LA1), 20.4 kDa (LA2), 28.9 kDa (LA3), 48.4 kDa (LA4), 68.4 kDa (LA5) or 119.2 kDa (LA6) were used. As shown in FIG. 5, the peaks of the protein standards appeared in order of increasing migration time corresponding to proteins of increasing size. Lower marker (LM) appeared initially at low migration time.

Instrument

Microchip capillary electrophoresis was performed using ProteinEXact™ assay or Pico Protein Express Assay on LabChip® GXII, LabChip® GXII Touch or LabChip® GXII Touch HT system (PerkinElmer, Hopkinton, MA). The LabChip® GXII Touch Capillary Electrophoresis System uses a single sipper microfluidic chip for protein separation including automations of electrophoretical separation and analyzing. The samples were loaded to 24-, 96- or 384-well microplates (or "plates") for the analysis. The optics of the system can detect the laser-induced fluorescent signal. The assay function of the system automatically analyzes the data to provide relative protein concentration, molecular size, and percent purity using ladder and marker calibration standards. The system can separate the proteins based on size with resolution in the range of from 14 to 200 kDa. The sensitivity of Protein Pico Assay is equivalent to silver stain. The sample can be analyzed in 42 seconds for Pico Protein Express or 65 seconds for ProteinEXact™. The throughput is up to 384 samples for Pico Protein Express or 96 samples for ProteinEXact™, per chip prep.

Example 1. Characterization of Capsid Viral Proteins Using Microchip Capillary Electrophoresis in Combination with Hydrophobic Dye The capsid viral proteins were analyzed using microchip capillary electrophoresis in combination with a hydrophobic dye. The capsid viral proteins were analyzed and characterized using LabChip® GXII Touch HT system (PerkinElmer) in combination with the ProteinEXact™ assay (PerkinElmer). The ProteinEXact™ assay was run according to the manufacturer's instructions (PerkinElmer, Hopkinton, MA, ProteinEXact™ HR Assay User Guide for LabChip® GXII Touch). Protein Clear HR dye in the reagent kit was added to ProteinEXact™ Gel matrix for protein detection. The LabChip® GXII Touch Capillary Electrophoresis System uses a single sipper microfluidic chip for protein separation including automations of staining, destaining, electrophoretical separation and analyzing. It also utilizes an on-system calibration step to enable reproducibility and sensitivities.

LabChip® GXII Touch HT system in combination with the ProteinEXact™ assay is a high throughput system for analysis and characterization of proteins using microfluidic capillary electrophoresis in the presence of SDS, for example, MCE-SDS. AAV serotype 8 (AAV8) was generated in HEK-293 cells and contained at least $5 \times 10^{12}$ genome copies/mL in D-PBS. Samples containing AAV8 were denatured prior to conducting the analysis, such as by heating the samples at about 75° C. When protein samples were prepared and denatured under non-reducing conditions, the protein samples were treated with iodoacetamide. When protein samples were prepared and denatured under reducing conditions, the protein samples were treated with DTT.

Figure 6A:
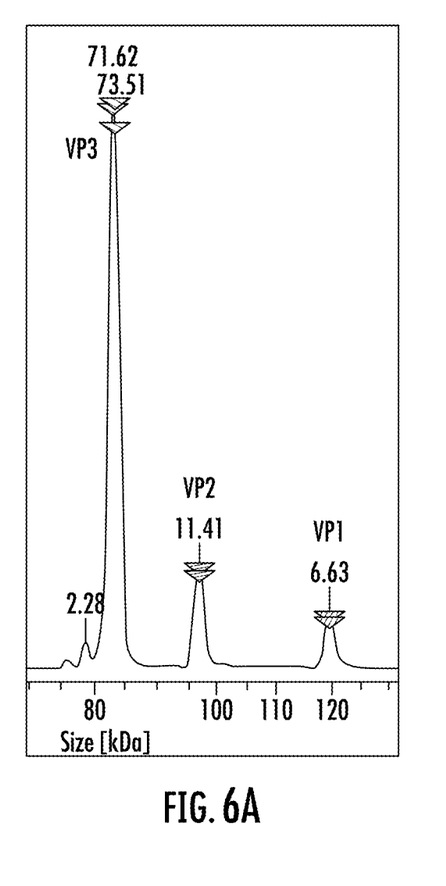
FIG. 6A shows the separation of capsid viral proteins of AAV8, such as VP1, VP2 and VP3, using capillary electrophoresis in combination with hydrophobic dye staining according to an exemplary embodiment.
Figure 6B:
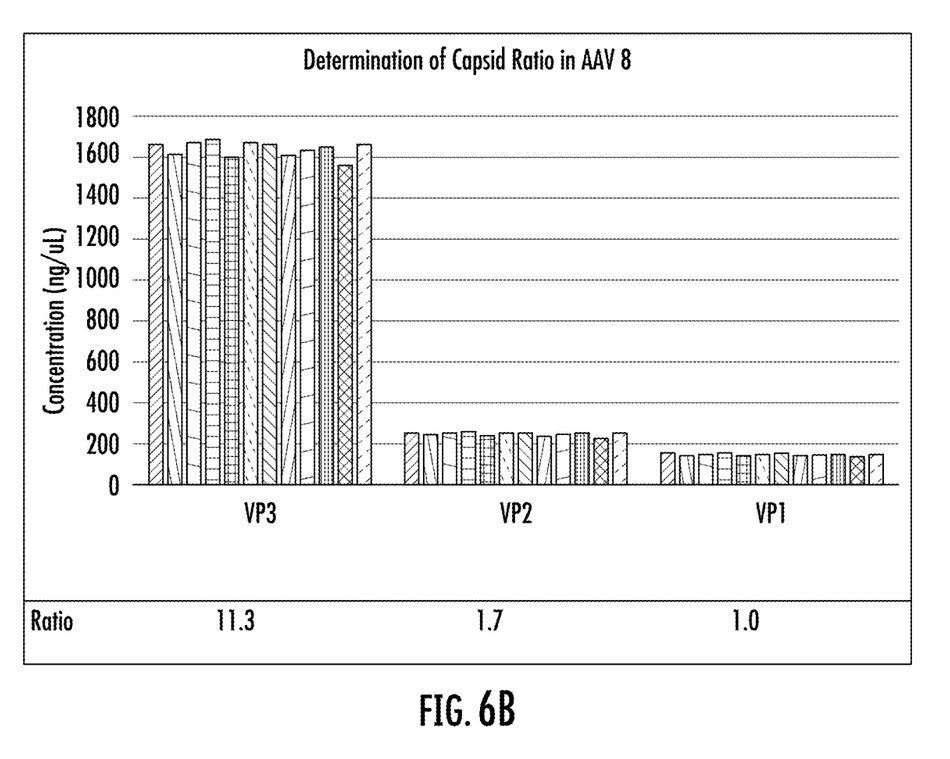
FIG. 6B shows the determination of a ratio of capsid viral proteins of AAV8, such as the ratio of VP1:VP2:VP3, using capillary electrophoresis in combination with hydrophobic dye staining according to an exemplary embodiment. Twelve electropherograms were overlaid to demonstrate the reproducibility of the assay.

The output of the ProteinEXact™ assay run on assay viewer is a relative electropherogram with quantitative analysis of size, fluorescence, concentration, and percent contribution of each individual protein relative to the total protein in the sample. The separated peaks in the electropherogram include VP1, VP2, VP3 and impurities. The corrected area under curve (AUC) for each protein was calculated, corresponding to concentration, which was used to determine the ratio of the capsid viral proteins in the sample. The capsid viral proteins of AAV8 were separated using capillary electrophoresis in combination with Protein Clear HR dye staining for protein detection as shown in FIG. 6A. The X axis in FIG. 6A is expressed as size in kDa. The Y axis represents fluorescence, corresponding to concentration. Twelve electropherograms were overlaid to demonstrate the reproducibility of the assay as shown in FIG. 6B. FIG. 6B shows the calculated ratio of VP1:VP2:VP3 based on the average concentration for each peak, which was normalized to VP1. As shown in FIG. 6B, the ratio of capsid viral proteins of AAV8, VP1:VP2:VP3, was calculated as 1.0:1.7:11.3. This VP1:VP2:VP3 ratio, 1.0:1.7:11.3, is significantly deviated from the theoretical ratio of 1:1:10.

Example 2. Characterization of Capsid Viral Proteins Using Microchip Capillary Electrophoresis in Combination with Lysine-Conjugation Dyes The AAV capsid viral proteins were quantified and characterized using microchip capillary electrophoresis in combination with lysine-conjugation fluorescent dyes. The AAV capsid viral proteins were analyzed and characterized using LabChip® GXII Touch HT system in the presence of LDS in combination with Pico Protein Express Assay. The Pico Protein Express Assay including protein labelling was conducted according to the manufacturer's instructions, with further optimizations as shown in Table 1. The Pico Protein Express labeling dye in the reagent kit was used to label capsid viral proteins by conjugating to free amines, such as lysine residues of the capsid viral proteins. The LabChip® GXII Touch HT Capillary Electrophoresis System used a single sipper microfluidic chip for protein separation including automations of electrophoretical separation and analyzing. It also utilized an on-system calibration step to enable reproducibility and sensitivities.

AAVs were generated in HEK-293 cells and reported to contain at least $5 \times 10^{12}$ genome copies/mL in D-PBS. AAV8 samples containing different payloads, payload A, B or C, were used for the analysis. The AAV8 samples were labeled with the Pico Protein Express labeling dye under reduced or non-reduced conditions according to the manufacturer's instructions as shown in FIG. 3 and FIG. 4, with the Pico 1.0 optimizations detailed in Table 1. When protein samples were prepared and denatured under non-reducing conditions, the protein samples were treated with iodoacetamide. When protein samples were prepared and denatured under reducing conditions, the protein samples were treated with DTT. The AAV8 sample was mixed with labeling buffer containing LDS with or without reducing agent. Subsequently, samples containing AAV8 were denatured by heating the samples at 75° C. for 10 minutes. The Pico Protein Express labeling dye was added to the denatured AAV8 samples with mixing for one minute followed by incubation at 35° C. for 30 minutes in the dark. A stop solution was added to the sample to terminate the dye conjugation reaction. The denatured and labelled AAV8 samples were subjected to analysis using Pico Protein Express Assay in LabChip® GXII Touch HT Capillary Electrophoresis System.

Figure 7:
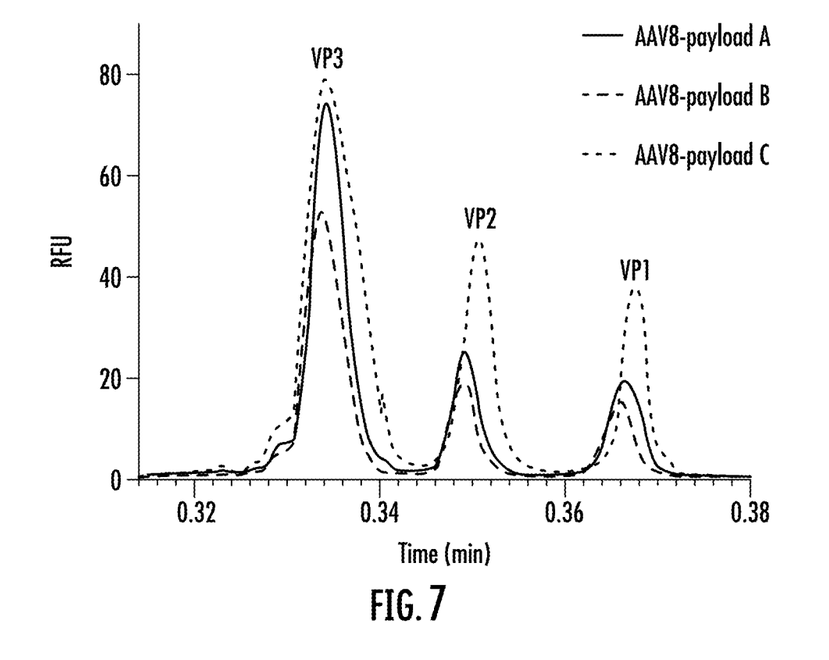
FIG. 7 shows the separation of labelled capsid viral proteins of AAV8 using capillary electrophoresis in combination with lysine-conjugation dyes according to an exemplary embodiment.

The output of the Pico Protein Express Assay run on assay viewer is a relative electropherogram with quantitative analysis of size, fluorescence, and percent contribution of each individual protein relative to the total protein in the sample. The separated peaks in the electropherogram include VP1, VP2, VP3 and impurities. The labelled capsid viral proteins of AAV8 were separated using capillary electrophoresis as shown in FIG. 7. The X axis in FIG. 7 is expressed as migration time. The Y axis represents fluorescence (RFU), corresponding to concentration. The corrected area under curve (AUC) for each protein was calculated, corresponding to concentration, which was used to determine the ratio of the capsid viral proteins in the sample.

Table 2 shows the calculated ratios of the capsid viral proteins, VP1:VP2:VP3, for three AAV8 samples using Pico Express Assay Pico 1.0. Table 2 also lists the corresponding lysine number and migration time for each capsid viral protein. Table 3 shows the corresponding determined molecular weights of VP1, VP2 and VP3. Since each capsid viral protein has different lysine contents, the ratios were normalized using the content of lysine residues and corrected with migration time in microchip channels as shown in Table 4. The ratios were normalized to VP1.

TABLE 1

| Pico Protein Express Assay optimized parameters | | |
| --- | --- | --- |
| Method Parameters | Pico 1.0 | Pico 2.0 |
| Non-reducing buffer | 100 mM sodium phosphate + 1% LDS + 165 mM IAM | 120 mM sodium phosphate + 1.2% LDS + 200 mM IAM |
| Non-reducing pH | 6-9 | 8 |
| Reducing buffer | 100 mM sodium phosphate + 1% LDS + 140 mM DTT | 120 mM sodium phosphate + 1.2% LDS + 80 mM DTT |
| Reducing pH | 9 | 8 |
| AAV8 denaturing temperature (° C.) | 75; 95 | 65 |
| Other AAV serotypes denaturing temperature (° C.) | 95 | 95 |
| Working concentration (mg/mL) | 0.1 | 0.1 |
| Dye concentration (μM) | 10 | 16 |
| Ladder labeling | Fresh (within 4 hours) | Pre-made/frozen at −20 ° C. |
| Separation time/sample (s) | 42 | 65 |

TABLE 2

Capsid viral protein ratios using Pico 1.0

| Pico 1.0 Ratio | VP3 | VP2 | VP1 |
|---|---|---|---|
| AAV8-payload A | 4.4 | 1.2 | 1 |
| AAV8-payload B | 4.3 | 1.1 | 1 |
| AAV8-payload C | 4 | 1.4 | 1 |
| Lysine number | 17 | 22 | 32 |
| Migration time (min) | 0.334 | 0.351 | 0.368 |

TABLE 3

Determined molecular weights of the capsid viral proteins

| MW (kDa) | VP3 | VP2 | VP1 |
|---|---|---|---|
| AAV8-payload A | 72.5 | 88.8 | 109.1 |
| AAV8-payload B | 72.5 | 90.3 | 110.6 |
| AAV8-payload C | 73.8 | 92.3 | 113.6 |

TABLE 4

Normalized and corrected protein ratios using Pico 1.0

| Normalized and Corrected Pico 1.0 Ratio | VP3 | VP2 | VP1 |
|---|---|---|---|
| AAV8-payload A | 9.1 | 1.8 | 1.0 |
| AAV8-payload B | 8.9 | 1.7 | 1.0 |
| AAV8-payload C | 8.3 | 2.1 | 1.0 |

In addition, the further optimized Pico Express Assay Pico 2.0 as detailed in Table 1 was used to assess the ratios of the capsid viral proteins. Table 5 shows the calculated ratios of the capsid viral proteins, VP1:VP2:VP3, for three AAV8 samples using Pico Express Assay Pico 2.0. Table 5 also lists the corresponding lysine number for each viral protein. Since each capsid viral protein has different lysine contents, the protein ratios were normalized using the content of lysine residues and corrected with migration time in microchip channels as shown in Table 6.

TABLE 5

Capsid viral protein ratios using Pico 2.0

| Pico 2.0 Ratio | VP3 | VP2 | VP1 |
|---|---|---|---|
| AAV8-payload A | 5.2 | 1 | 1 |
| AAV8-payload B | 5.1 | 1.1 | 1 |
| AAV8-payload C | 5.0 | 1.3 | 1 |
| Lysine number | 17 | 22 | 32 |

TABLE 6

Normalized and corrected protein ratios for Pico 2.0

| Normalized and Corrected Pico 2.0 Ratio | VP3 | VP2 | VP1 |
|---|---|---|---|
| AAV8-payload A | 9.8 | 1.4 | 1.0 |
| AAV8-payload B | 9.3 | 1.5 | 1.0 |
| AAV8-payload C | 9.9 | 2.0 | 1.0 |

These protein ratios were normalized to VP1. The optimization using Pico 2.0 provided improvement in signal intensity and data reproducibility, and is suitable for samples with lower concentrations.

What is claimed:

1. A method of measuring the amounts of capsid viral proteins in a sample containing at least one AAV vector used for nucleic acid delivery, comprising:
   (a) denaturing the sample containing at least two proteins in a denaturation solution at a temperature of at least about 60° C.;
   (b) labelling the denatured at least two proteins with a lysine-conjugation dye;
   (c) applying microchip capillary electrophoresis to the labelled at least two proteins to obtain an electropherogram showing a separation profile and amounts of at least two proteins from the AAV vector in the sample.

2. The method of claim 1, further comprising normalizing a quantification ratio based on lysine contents of the at least two proteins, wherein the quantification ratio is the ratio between the amounts of the at least two proteins from the AAV vector.

3. The method of claim 2, further comprising correcting the quantification ratio based on a migration time of the separation profile.

4. The method of claim 1, wherein the lysine-conjugation dye is an amine-reactive fluorescent dye.

5. The method of claim 1, wherein the lysine-conjugation dye comprises an active ester, an isothiocyanate, or a sulfonyl chloride.

6. The method of claim 1, wherein the lysine-conjugation dye comprises an active ester, wherein the active ester includes a succinimidyl ester, a sulfosuccinimidyl ester, a tetrafluorophenyl ester, or a sulfodichlorophenol ester.

7. The method of claim 1, wherein the at least one AAV vector comprises viral protein 1 (VP1), viral protein 2 (VP2) and viral protein 3 (VP3).

8. The method of claim 1, wherein the denaturation solution comprises a detergent.

9. The method of claim 1, wherein the denaturation solution comprises lithium dodecyl sulfate (LDS) or sodium dodecyl sulfate (SDS).

* * * * *